(12) United States Patent
Matsumoto

(10) Patent No.: US 10,716,456 B2
(45) Date of Patent: Jul. 21, 2020

(54) MANIPULATION ROPE

(71) Applicant: TOKUSEN KOGYO CO., LTD., Ono, Hyogo (JP)

(72) Inventor: Keiji Matsumoto, Ono (JP)

(73) Assignee: TOKUSEN KOGYO CO., LTD., Ono, Hyogo (JP)

( * ) Notice: Subject to any disclaimer, the term of this patent is extended or adjusted under 35 U.S.C. 154(b) by 0 days.

(21) Appl. No.: 15/570,833

(22) PCT Filed: Apr. 22, 2016

(86) PCT No.: PCT/JP2016/062747
§ 371 (c)(1),
(2) Date: Oct. 31, 2017

(87) PCT Pub. No.: WO2016/208263
PCT Pub. Date: Dec. 29, 2016

(65) Prior Publication Data
US 2018/0148893 A1   May 31, 2018

(30) Foreign Application Priority Data
Jun. 26, 2015 (JP) ................................. 2015-128586

(51) Int. Cl.
*A61B 1/00* (2006.01)
*A61B 17/12* (2006.01)
(Continued)

(52) U.S. Cl.
CPC ................ *A61B 1/00* (2013.01); *A61B 1/005* (2013.01); *A61B 1/00064* (2013.01);
(Continued)

(58) Field of Classification Search
CPC .......... D07B 1/06; D07B 1/0673; D07B 1/22; D07B 5/005; A61B 1/00; A61B 1/005; A61B 17/12; A61B 17/28; F16C 1/00
See application file for complete search history.

(56) References Cited

U.S. PATENT DOCUMENTS 5,609,014 A * 3/1997 Obara .................. D07B 1/0626
                                                        57/212
5,766,184 A   6/1998 Matsuno et al.
(Continued)

FOREIGN PATENT DOCUMENTS

CN     104415448 A    3/2015
EP      2845620 A1    3/2015
(Continued)

OTHER PUBLICATIONS https://www.cortlandcompany.com/sites/default/files/downloads/media/technical-fact-sheets-spectra-12-strand.pdf (Year: 2006).*
(Continued)

*Primary Examiner* — Shaun R Hurley
(74) *Attorney, Agent, or Firm* — Dickinson Wright PLLC

(57) ABSTRACT

A manipulation rope having an excellent torque transmittability is provided. A manipulation rope 2 is a rope 2 that is advantageously used as a manipulation rope for a medical instrument, and includes a side wire 6 or a side strand which is an outermost layer, the side wire 6 or the side strand having a spiral shape in which a flatness that is an aspect ratio obtained by a major axis being divided by a minor axis is greater than 1.00 and not greater than 1.10. An elongation of the rope at a time when a tensile load that is 1.0% of a breaking load is applied, is preferably not less than 0.04% and preferably not greater than 0.10%.

5 Claims, 7 Drawing Sheets

(51) Int. Cl.
*A61B 17/28* (2006.01)
*D07B 1/06* (2006.01)
*F16C 1/00* (2006.01)
*A61B 1/005* (2006.01)
*D07B 1/14* (2006.01)
*A61M 25/09* (2006.01)
*F16C 1/20* (2006.01)
*D07B 5/00* (2006.01)
*F16C 1/02* (2006.01)

(52) U.S. Cl.
CPC .............. *A61B 17/12* (2013.01); *A61B 17/28* (2013.01); *D07B 1/0673* (2013.01); *D07B 1/0693* (2013.01); *D07B 1/14* (2013.01); *F16C 1/00* (2013.01); *A61M 2025/09191* (2013.01); *D07B 1/0633* (2013.01); *D07B 1/0646* (2013.01); *D07B 5/005* (2013.01); *D07B 2201/204* (2013.01); *D07B 2201/2008* (2013.01); *D07B 2201/2021* (2013.01); *D07B 2201/2037* (2013.01); *D07B 2201/2039* (2013.01); *D07B 2201/2059* (2013.01); *D07B 2205/3028* (2013.01); *D07B 2205/3032* (2013.01); *D07B 2207/4063* (2013.01); *D07B 2207/4072* (2013.01); *D07B 2501/2084* (2013.01); *F16C 1/02* (2013.01); *F16C 1/20* (2013.01)

(56) References Cited

U.S. PATENT DOCUMENTS

| | | | | |
|---|---|---|---|---|
| 2006/0021428 A1* | 2/2006 | Metni | ................... | A63G 31/00 73/147 |
| 2007/0193644 A1* | 8/2007 | Verreet | ................... | B22F 5/12 140/112 |
| 2010/0133046 A1* | 6/2010 | Allwardt | ................... | B66B 7/08 187/251 |
| 2010/0200143 A1* | 8/2010 | Okamoto | ............... | B29D 30/48 152/539 |
| 2014/0295184 A1* | 10/2014 | Grabandt | ............... | D07B 1/025 428/371 |
| 2018/0105981 A1* | 4/2018 | Matsumoto | ........... | A61M 25/09 |
| 2018/0161053 A1* | 6/2018 | Matsumoto | ........ | A61B 1/00121 |

FOREIGN PATENT DOCUMENTS

| | | |
|---|---|---|
| FR | 2533744 A1 | 3/1984 |
| JP | 1-62396 U | 4/1989 |
| JP | H01-062396 U | 4/1989 |
| JP | H08-126648 A | 5/1996 |
| JP | H09-256285 A | 9/1997 |
| JP | 2003-155676 A | 5/2003 |
| JP | 3101207 U | 2/2004 |
| JP | 2005-013296 A | 1/2005 |
| JP | 2006-283259 A | 10/2006 |
| JP | 2008-017954 A | 1/2008 |
| JP | 2008-155052 A | 7/2008 |
| JP | 2011-006803 A | 1/2011 |
| JP | 2012-157378 A | 8/2012 |

OTHER PUBLICATIONS

International Search Report dated Nov. 10, 2015 for corresponding JP Patent Application No. 2015-128586.

European Search Report dated Jan. 30, 2019, which issued in the corresponding European Patent Application No. 16814034.1.

* cited by examiner

MANIPULATION ROPE

TECHNICAL FIELD

The present invention relates to manipulation ropes that can be used also for, for example, medical instruments.

BACKGROUND ART

As a medical instrument equipped with a manipulation rope, for example, an endoscope treatment instrument disclosed in JPH8-126648 is known. In the endoscope treatment instrument, an operation unit being held by hand and a treatment unit provided at its leading end are connected by a manipulation wire rope having torque transmittability. An operator inserts the treatment unit into a body cavity of a patient and operates the operation unit, whereby an operating force thereof is transmitted to the treatment unit by the manipulation wire rope. The manipulation wire rope allows a pushing force, a pulling force, and a rotational force (torque) to be transmitted from the operation unit to the treatment unit. By the transmitted force, a portion, of a body, to be treated can be subjected to medical treatment.

The manipulation wire rope is required to have not only transmittability of pushing and pulling force, but also an excellent torque transmittability (rotation followability) according to application of the manipulation wire rope. In a case where a torque transmittability or the like of the manipulation wire rope is insufficient, an operation of the operation unit is not reproduced by the treatment unit. Furthermore, particularly in the field of medical devices, the manipulation wire rope is required to have flexibility according to the diameter of the medical device being reduced.

A manipulation wire rope used for a medical treatment instrument is disclosed in JP2005-13296. The wire rope is structured such that, by, for example, wires in the outer layer and wires in the inner layer being stranded in a parallel lay, the wires adjacent to each other are brought into contact with each other as closely as possible along the rope longitudinal direction. This structure is adopted in order to inhibit reduction of an operating force and an operation amount from an operation unit to a treatment unit. However, in the field of medical devices, torque transmittability, flexibility, and the like of the manipulation wire rope are required to be further improved.

CITATION LIST

Patent Literature

Patent Literature 1: JPH8-126648
Patent Literature 2: JP2005-13296

SUMMARY OF THE INVENTION

Problems to be Solved by the Invention

The present invention is made in view of the aforementioned circumstances, and an object of the present invention is to provide a manipulation rope having an excellent torque transmittability.

Solutions to the Problems

A manipulation rope of the present invention includes a side wire or a side strand which is an outermost layer, the side wire or the side strand having a spiral shape in which a flatness that is an aspect ratio obtained by a major axis being divided by a minor axis is greater than 1.00 and not greater than 1.10.

Preferably, an elongation of the rope at a time when a tensile load that is 1.0% of a breaking load is applied, is not less than 0.04% and not greater than 0.10%.

Preferably, the flatness is not less than 1.01 and not greater than 1.05.

Preferably, a strand angle of the side wire or the side strand is not less than 15°.

Advantageous Effects of the Invention

The manipulation rope of the present invention has an excellent torque transmittability.

DESCRIPTION OF EMBODIMENTS

The following will describe in detail the present invention based on preferred embodiments with reference where appropriate to the accompanying drawing.

Figure 1:
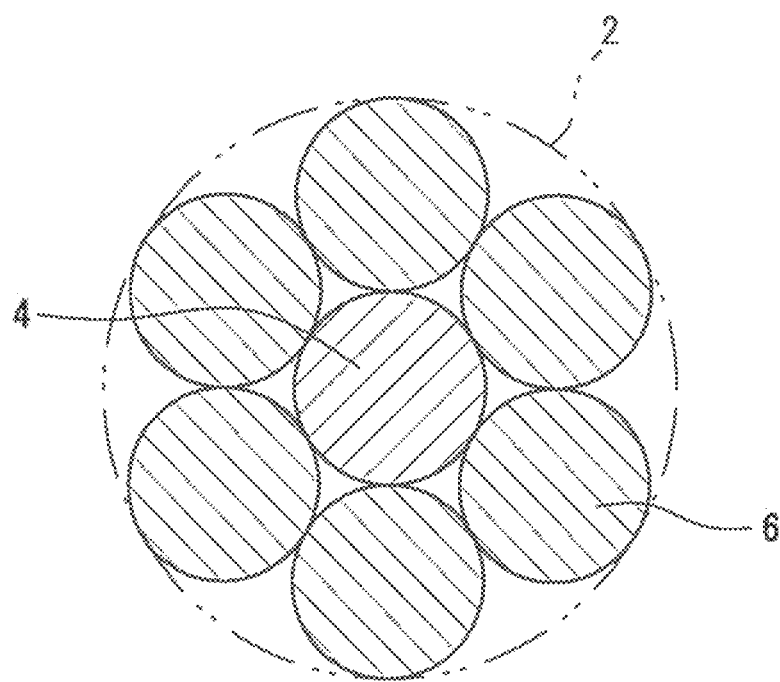
FIG. 1 is a transverse cross-sectional view of a manipulation rope according to one embodiment of the present invention.
Figure 2:
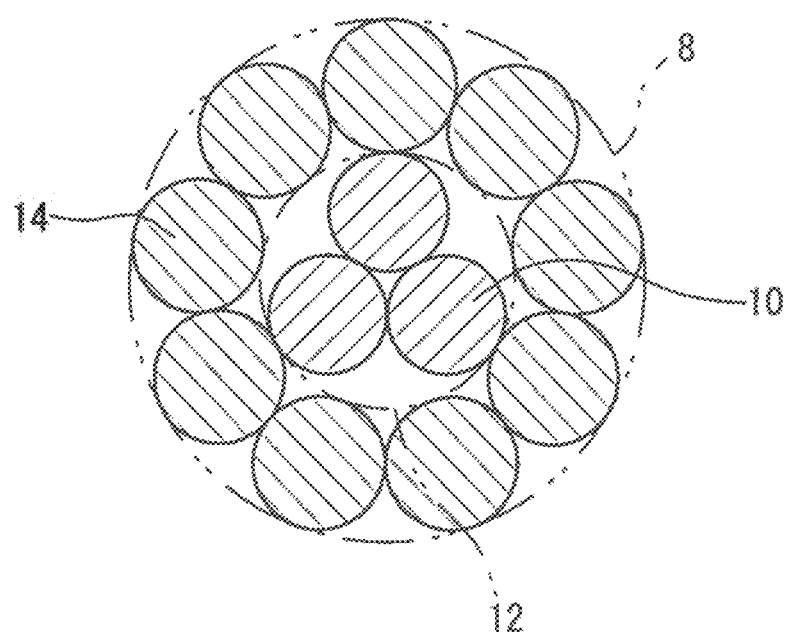
FIG. 2 is a transverse cross-sectional view of a manipulation rope according to another embodiment of the present invention.
Figure 3:
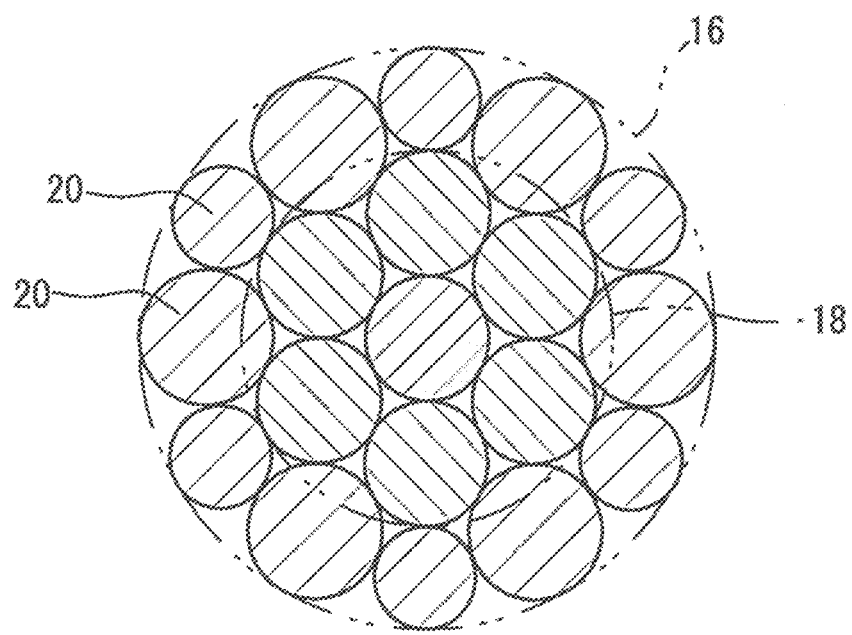
FIG. 3 is a transverse cross-sectional view of a manipulation rope according to still another embodiment of the present invention.

FIG. 1 to FIG. 3 illustrate a plurality of examples of manipulation wire ropes (hereinafter, each simply referred to also as rope) according to the present invention. Ropes 2, 8, 16 each include a strand obtained by a plurality of wires being stranded. The present invention is not limited to the structure of the embodiment shown in each of FIG. 1 to FIG. 3.

The rope 2 shown in FIG. 1 has a 1+6 layer stranded structure which includes one core wire (core) 4 and six wires (each of which is also referred to as side wire) 6 in the outermost layer. The rope 8 shown in FIG. 2 has a 3+9 layer stranded structure which includes a core strand 12 formed from three wires 10 and nine side wires 14. The rope 16 shown in FIG. 3 has a 1+6+12 layer stranded structure which includes: a core strand 18 which is a 1+6 layer stranded inner layer; and 12 side wires 20. In the rope 16, the side wires 20 have different diameters such that the transverse cross-sectional shape of the rope 16 is close to a circular shape. However, the rope 16 is not limited to one having such a structure, and all the side wires 20 may have the equal diameter. The rope 2, 8, 16 has a stranded structure suitable to a manipulation rope used for a medical instrument. However, the rope 2, 8, 16 is not limited to such a manipulation rope.

The rope 2, 8, 16 of the embodiment can be used for a medical instrument. The rope is attached to a medical instrument for manipulation such that, for example, the proximal end portion of the rope is connected to an operation unit, being held by hand, of the medical instrument, and the leading end portion of the rope is connected to a treatment unit. Torque and pushing and pulling force applied to the proximal end portion are transmitted to the leading end portion, and the treatment unit is allowed to perform a treatment operation.

In the present embodiment, the wire of the rope 2, 8, 16 is formed from an austenitic stainless steel such as SUS304 and SUS316 or the like, a nickel-titanium alloy, or the like. Needless to say, the material of the wire is not limited to such a material. The tensile strength of the material of the wire is preferably not less than 2000 MPa, more preferably not less than 2500 MPa, and particularly preferably not less than 2800 MPa.

The shape of a spiral of the side wire 6, 14, 20 or the side strand which is an outermost layer is not completely circular but ellipsoidal or oval when the rope 2, 8, 16 is disassembled (disentangled). In other words, the spiral is a so-called flattened spiral.

In the side wire 6, 14, 20 or the side strand, the flatness (also referred to as aspect ratio) is preferably greater than 1.00 and preferably not greater than 1.10. The flatness represents an aspect ratio, of the above-described flattened spiral of the disentangled side wire or side strand, obtained by dividing the major axis by the minor axis. An example of a method for measuring the diameter of the spiral will be described below. On a projector, the disentangled side wire or side strand is rotated around the center axis thereof. In this process, the diameters of the spiral are measured at any plurality of angular positions (for example, five positions). The plurality of angular positions are preferably spaced from each other at equiangular intervals. The greatest value among the plurality of measured values is determined as the major axis. The diameter of the spiral which is measured in the direction obtained by 90° phase rotation around the center axis of the side wire or the side strand being performed from the direction in which the major axis is measured, is determined as the minor axis. In the disentangled side wire or side strand, a plurality of spirals are formed continuously along the axial direction thereof. Therefore, as each diameter in the 90° intersecting direction, an average of a plurality of measured values (for example, at any 10 positions) is adopted.

When the flatness is in the above-described range, the rope becomes flexible and is easily bent. Further, friction between the side wires or between the side strands is increased, and friction between the side wire or the side strand and the core wire or the core strand is reduced, thereby reducing energy loss in transmission of rotation of the rope. By this action, transmission of rotational force from the proximal end to the leading end is facilitated, and torque transmittability is improved.

When the flatness is not greater than 1.00, friction between the side wire or the side strand and the core wire or the core strand is increased, so that energy loss in transmission of rotation of the rope may be increased. Meanwhile, when the flatness is greater than 1.10, a so-called open structure is caused, and the rope may be difficult to stably manufacture. In this viewpoint, the flatness is preferably not less than 1.01 and preferably not greater than 1.05.

An initial elongation of the rope 2, 8, 16 is preferably not less than 0.04% and preferably not greater than 0.10%. The initial elongation of the rope is obtained by an elongation (increase rate of length) of a rope at a time when a tensile load that is 1.0% of a breaking load of the rope is applied being represented as a percentage.

The rope having a great initial elongation is flexible and easily bent. That is, the rope having a great initial elongation has a small longitudinal elastic modulus (Young's modulus). When the initial elongation is less than 0.04%, friction between the side wire or the side strand and the core wire or the core strand is increased, so that energy loss in transmission of rotation of the rope may be increased. Meanwhile, when the initial elongation is greater than 0.10%, the rope tends to have a so-called open structure, and the rope may be difficult to stably manufacture.

The initial elongation is confirmed by a tensile testing for a rope to be tested. The tensile testing can be performed in compliance with the standard of JISZ2241 (2011). Initially, a breaking load of the rope to be tested is measured. Then, the rope to be tested is attached to the tester, and a tensile load is applied thereto. At a time when the tensile load becomes 1.0% of the breaking load, increase of the gauge length that is set in the axial direction of the rope to be tested is measured. The percentage of the increase relative to the original gauge length is set as the initial elongation.

A strand angle of the side wire 6, 14, 20 or the side strand of the rope 2, 8, 16 is preferably not less than 15°. In the rope in which the strand angle is not less than 15°, the initial elongation that is not less than 0.04% can be easily obtained. The strand angle is an angle between the wire or the strand, and the center axis of the rope or the strand. In the description herein, the strand angle is an angle between the side wire or the side strand, and the center axis of the rope.

A process for manufacturing the rope will be briefly described below. Initially, each wire of the rope is adjusted in the wire drawing process step such that a required tensile strength can be obtained. Then, preforming is performed for the side wire or the side strand by a preformer in the wire stranding process step such that a required flatness can be obtained. In particular, the preforming (forming) is performed such that the spiral of the side wire or the side strand has a flattened transverse cross-section. In the heat treatment process step for the rope, not batch processing but continuous processing is performed. Specifically, the rope, to be processed, which passes through a heat treatment furnace is tensioned at an inlet and an outlet of the heat treatment furnace. Thus, the straightness of the rope is improved. Further, the flatness of the side wire or the side strand is determined.

EXAMPLES

Hereinafter, effects of the present invention will become apparent according to examples. However, the present invention should not be restrictively construed based on the description of examples.

Examples 1 to 8

Manipulation wire ropes of examples 1 to 8 each having the structure shown in FIG. 1 were obtained. Each of the ropes was a wire rope for a medical device. A material of each of the wires was SUS304 austenitic stainless steel. The outer diameter (cord diameter) of the rope was 0.8 mm, the outer diameter of the core wire was 0.28 mm, and the outer diameter of the side wire was 0.26 mm. Each wire had the tensile strength of 2812 MPa. Each rope had a 1+6 layer stranded structure, and a stranding pitch in each rope was 5.8 mm. The temperature in the heat treatment for the rope of each of examples 1 to 8 was 550° C. The flatness and the initial elongation of the side wire of the rope of each of examples 1 to 8 were as indicated in Table 1 and Table 2.

Comparative Example 1

A manipulation wire rope of comparative example 1 was obtained in the same manner as in example 1 except that the flatness and the initial elongation were as indicated in Table 2. The side wire of the rope of comparative example 1 was not flattened.

Comparative Example 2

A manipulation wire rope of comparative example 2 was obtained in the same manner as in example 1 except that the flatness and the initial elongation were as indicated in Table 2, and the diameter of the cord was much greater than 0.8 mm. As indicated in Table 2, the flatness of the rope of comparative example 2 was 1.50, and a so-called open structure in which multiple gaps were generated among the wires, was caused. Therefore, the diameter of the cord was much greater than 0.8 mm. Such a rope of comparative example 2 was not suitable as a manipulation wire rope for a medical device, and it was determined that this rope was not able to be used as a manipulation wire rope for a medical device.

Comparative Example 3

Comparative example 3 was a manipulation wire rope according to conventional art. The manipulation wire rope of comparative example 3 was the same as in example 1 except that the flatness and initial elongation were as indicated in Table 2. The side wire of the rope of comparative example 3 was not flattened.

TABLE 1

Evaluation of torque transmittability

| | Ex. 1 | Ex. 2 | Ex. 3 | Ex. 4 | Ex. 5 | Ex. 6 |
|---|---|---|---|---|---|---|
| Flatness | 1.005 | 1.01 | 1.05 | 1.01 | 1.01 | 1.01 |
| Initial elongation (%) | 0.05 | 0.05 | 0.05 | 0.03 | 0.04 | 0.10 |
| Torque transmittability (index) | 67.0 | 47.2 | 48.9 | 65.2 | 55.9 | 49.0 |

TABLE 2

Evaluation of torque transmittability

| | Ex. 7 | Ex. 8 | Comp. Ex. 1 | Comp. Ex. 2 | Comp. Ex. 3 |
|---|---|---|---|---|---|
| Flatness | 1.02 | 1.10 | 1.00 | 1.50 | 1.00 |
| Initial elongation (%) | 0.07 | 0.05 | 0.05 | 0.05 | 0.02 |
| Torque transmittability (index) | 45.1 | 60.7 | 96.0 | Not usable | 100 |

Evaluation of Torque Transmittability

Torque transmittability is evaluated on the basis of difference, between a rotation angle on the proximal end side (corresponding to the operation unit) and a rotation angle on the leading end side (corresponding to the treatment unit), obtained when the proximal end side portion of each rope was rotated. For the rope of each of examples and comparative examples, the following torque transmittability evaluation test was performed.

Figure 4:
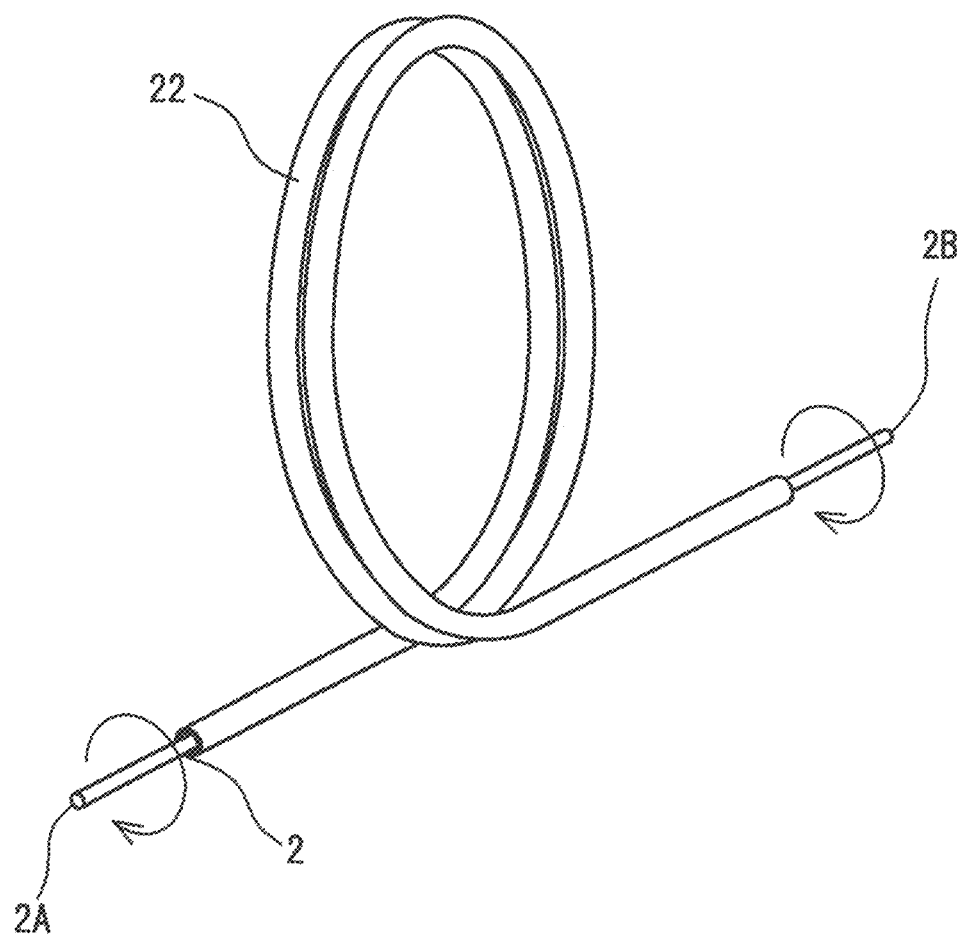
FIG. 4 is a perspective view illustrating an outline of a torque transmittability evaluation testing method for a manipulation rope.

As shown in FIG. 4, a dual spiral having the diameter of 200 mm was formed in the rope of each of examples 1 to 8 and comparative examples 1 to 3. The dual spiral was formed by, for example, a rope 2 to be tested being inserted into a small-diameter pipe 22 which had a dual spiral shape having the diameter of 200 mm so as to be straight on both end sides. A rotational force around the center axis was applied to the proximal end side portion of the rope 2 to be tested, in a state where the rope 2 to be tested was inserted in the small-diameter pipe 22. While the rotational force was applied, a rotation angle on a proximal end side 2A of the rope 2 and a rotation angle on a leading end side 2B thereof were simultaneously measured.

Figure 5:
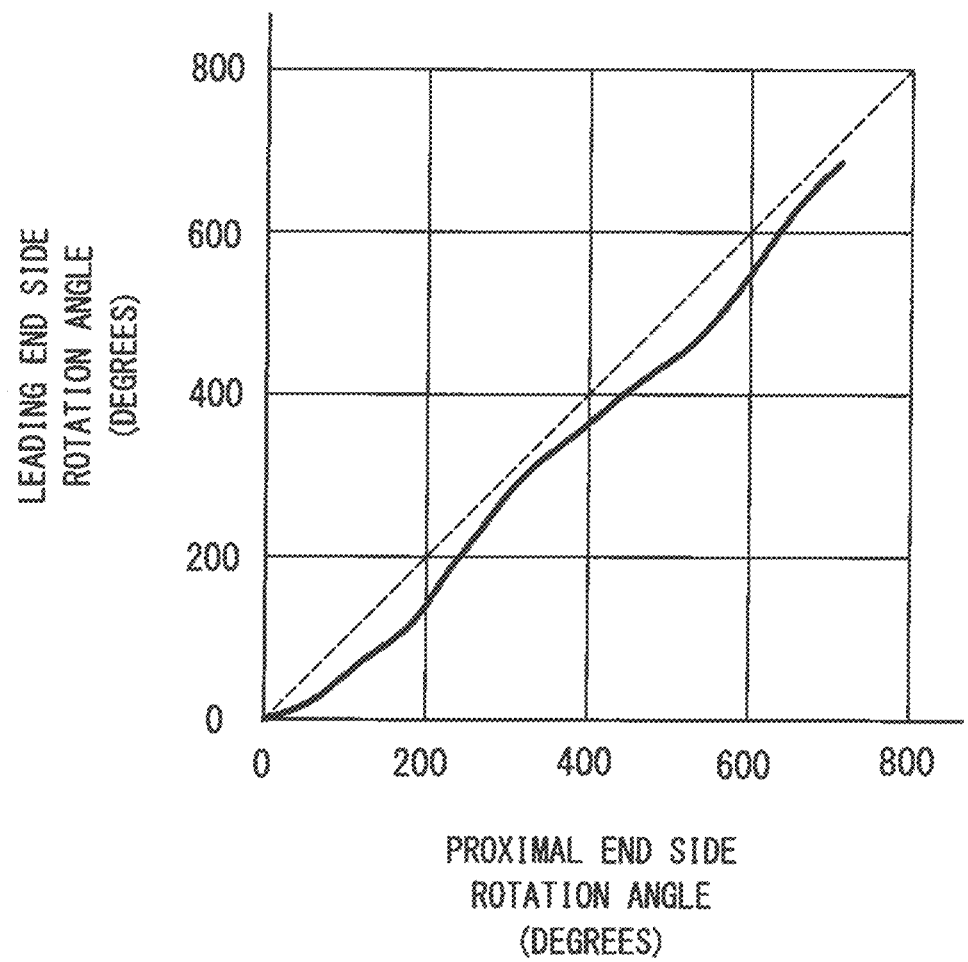
FIG. 5 shows a graph in which a rotation angle of a manipulation rope on a proximal end side and a rotation angle thereof on the leading end side at the same point of time are associated with each other.
Figure 6:
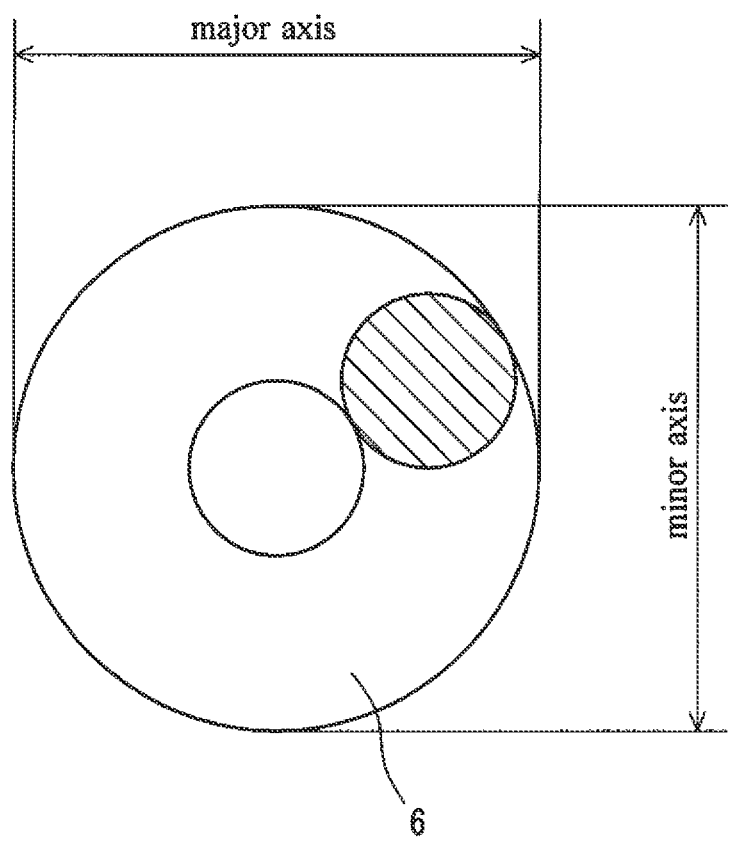
FIG. 6 is an illustration showing the major and minor axis.
Figure 7:
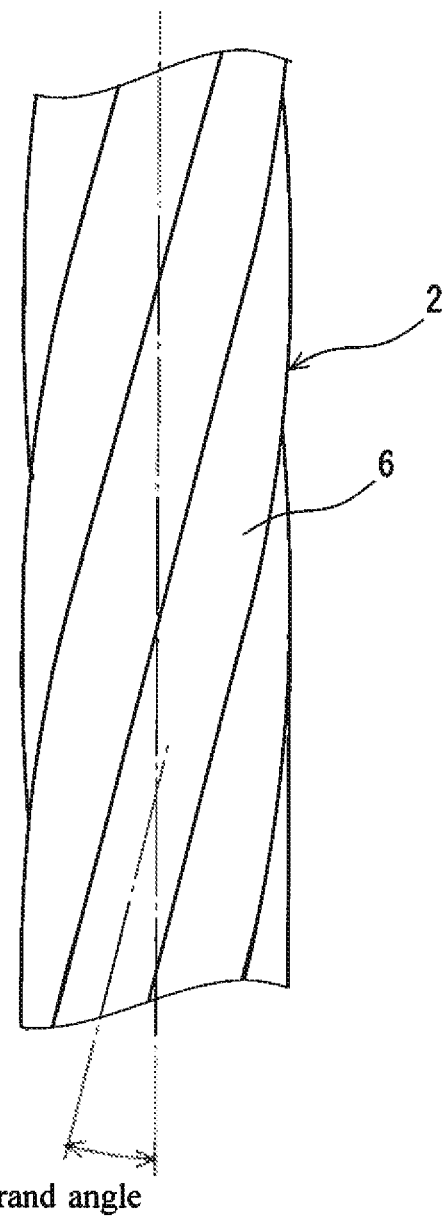
FIG. 7 is an illustration showing the strand angle.

FIG. 5 shows a graph in which the rotation angle on the proximal end side of the rope and the rotation angle on the leading end side thereof at the same point of time are associated with each other. In other words, FIG. 5 is a graph indicating a relationship between an input rotation angle and an output rotation angle in the manipulation rope. The unit of the angle is degree (°). In the graph, a broken line that extends from the originating point of 0° so as to be tilted by 45° relative to the horizontal axis and the vertical axis represents a straight line that indicates that difference between the rotation angle on the proximal end side and the rotation angle on the leading end side is zero in a range of ail the measured angles (range in which the input rotation angle is from 0° to about 720°). The difference, to be evaluated for the rope to be tested, between the rotation angle on the proximal end side and the rotation angle on the leading end side is represented as difference in the vertical axis direction between the 45° titled straight line and the measured value curve in the drawing. The difference in the rotation angle corresponds to the rotation angle on the proximal end side. In the drawing, for easy understanding, the difference in the rotation angle is indicated so as to be greater than the actual one. In the range in which the input rotation angle is from 0° to 720°, the greatest angular difference among the measured differences in the rotation angle is evaluated.

The greatest angular difference in the rope of each of examples 1 to 8 and comparative examples 1 to 3 is indicated in Table 1 and Table 2 as an index with the greatest angular difference of comparative example 3 being 100. The less the greatest angular difference is, the less the value of the index is and the more excellent the torque transmittability is.

As indicated in Table 1 and Table 2, the evaluation result clearly indicates that the present invention is superior.

INDUSTRIAL APPLICABILITY

The manipulation rope of the present invention is advantageously used as a manipulation rope for a medical instrument.

DESCRIPTION OF THE REFERENCE CHARACTERS 2, 8, 16 . . . manipulation wire rope
4 . . . core wire
6, 14, 20 . . . side wire 10 . . . wire
12, 18 . . . core strand

The invention claimed is:

1. A manipulation rope comprising a side wire or a side strand which is an outermost layer, and a core wire or core strand that generates friction with the side wire or side strand upon rotation of the manipulation rope, wherein the side wire or the side strand disentangled from the manipulation rope has a spiral shape in which a flatness has an aspect ratio obtained by a major axis being divided by a minor axis is greater than 1.00 and not greater than 1.10, and the side wire or side strand having a strand angle of not less than 15°, and where said manipulation rope is configured for transmitting torque.

2. The manipulation rope according to claim 1, wherein an elongation at a time when a tensile load that is 1.0% of a breaking load is applied, is not less than 0.04% and not greater than 0.10%.

3. The manipulation rope according to claim 1, wherein the flatness is not less than 1.01 and not greater than 1.05.

4. A medical instrument comprising:
- a manipulation rope comprising a side wire or a side strand which is an outermost layer, and a core wire or core strand that generates friction with the side wire or side strand upon rotation of the manipulation rope, wherein the side wire or the side strand disentangled from the manipulation rope has a spiral shape in which a flatness has an aspect ratio obtained by a major axis being divided by a minor axis is greater than 1.00 and not greater than 1.10, and where said manipulation rope is configured for transmitting torque;
- an operational unit configured to be held by hand and configured for connecting to the a proximal end of the manipulation rope, and
- a treatment unit configured for connecting to a leading end portion of the manipulation rope.

5. A manipulation rope comprising a side wire or a side strand which is an outermost layer, and a core wire or core strand that generates friction with the side wire or side strand upon rotation of the manipulation rope, wherein the side wire or the side strand disentangled from the manipulation rope has a spiral shape in which a flatness has an aspect ratio obtained by a major axis being divided by a minor axis is greater than 1.00 and not greater than 1.10, and where said manipulation rope is configured for transmitting torque and has an elongation at a time when a tensile load that is 1.0% of a breaking load is applied to said manipulation rope, is not less than 0.04% and not greater than 0.10%.

* * * * *